US012599746B2

(12) United States Patent
Velarde

(10) Patent No.: US 12,599,746 B2
(45) Date of Patent: Apr. 14, 2026

(54) CUFFED AND NON-CUFFED DIALYSIS CATHETER SYSTEMS AND METHODS

(71) Applicant: Franz E. Velarde, Harlingen, TX (US)

(72) Inventor: Franz E. Velarde, Harlingen, TX (US)

( * ) Notice: Subject to any disclaimer, the term of this patent is extended or adjusted under 35 U.S.C. 154(b) by 799 days.

(21) Appl. No.: 17/796,742

(22) PCT Filed: Feb. 4, 2021

(86) PCT No.: PCT/US2021/016562
§ 371 (c)(1),
(2) Date: Aug. 1, 2022

(87) PCT Pub. No.: WO2021/158753
PCT Pub. Date: Aug. 12, 2021

(65) Prior Publication Data
US 2024/0024623 A1 Jan. 25, 2024

Related U.S. Application Data

(60) Provisional application No. 62/969,846, filed on Feb. 4, 2020.

(51) Int. Cl.
*A61M 25/00* (2006.01)

(52) U.S. Cl.
CPC .... *A61M 25/0029* (2013.01); *A61M 25/0082* (2013.01); *A61M 2025/0019* (2013.01); *A61M 2025/0031* (2013.01)

(58) Field of Classification Search
CPC .......... A61M 25/0029; A61M 25/0082; A61M 2025/0019; A61M 2025/0031
See application file for complete search history.

(56) References Cited

U.S. PATENT DOCUMENTS

| | | | |
|---|---|---|---|
| 4,623,329 A | 11/1986 | Drobish et al. | |
| 4,717,379 A | 1/1988 | Ekholmer | |
| 5,378,230 A * | 1/1995 | Mahurkar | A61M 25/0023 |
| | | | 604/523 |
| 8,613,721 B2 | 12/2013 | Wulfman | |
| 10,357,601 B1 | 7/2019 | Flora et al. | |
| 2010/0256487 A1 | 10/2010 | Hawkins et al. | |

(Continued)

FOREIGN PATENT DOCUMENTS

WO WO 2019-005903 A1 1/2019

OTHER PUBLICATIONS

Extended European Search Report for related EP Application No. 21751095.7, dated Apr. 18, 2024.

(Continued)

*Primary Examiner* — Imani N Hayman
(74) *Attorney, Agent, or Firm* — Womble Bond Dickinson (US) LLP

(57) ABSTRACT

The present disclosure provides a catheter system including a plurality of fenestrations along the shaft of the catheter, wherein the fenestrations allow for continuous or intermittent infusion of antiseptics and/or antibiotics to avoid and treat bacterial colonization or infection of the subcutaneous tract and to minimize subcutaneous tunnel colonization and fibrin sheath in symptomatic or asymptomatic patients. The present catheter system can also include a removable abrasive component on the catheters tip to assist with mechanical debridement of subcutaneous tract and intravascular fibrin sheath.

16 Claims, 4 Drawing Sheets

(56)                    References Cited

U.S. PATENT DOCUMENTS

| 2014/0148788 | A1 |   | 5/2014 | Ryan et al. | |
|---|---|---|---|---|---|
| 2015/0018802 | A1 |   | 1/2015 | Zvuloni et al. | |
| 2015/0073327 | A1 |   | 3/2015 | Barrett et al. | |
| 2016/0367747 | A1 |   | 12/2016 | Loske | |
| 2017/0035997 | A1 |   | 2/2017 | Subramanian | |
| 2020/0001045 | A1 |   | 1/2020 | McIntyre | |
| 2020/0391006 | A1 | * | 12/2020 | Plessala .............. | A61M 5/1418 |

OTHER PUBLICATIONS

International Search Report and Written Opinion in PCT/US2021/016562, dated May 20, 2021.

* cited by examiner

CUFFED AND NON-CUFFED DIALYSIS CATHETER SYSTEMS AND METHODS

REFERENCE TO RELATED APPLICATION

The present patent application claims the benefit of U.S. Provisional Application No. 62/969,846, filed Feb. 4, 2020.

INCORPORATION BY REFERENCE

The disclosures made in U.S. Provisional Application No. 62/969,846, filed Feb. 4, 2020, are specifically incorporated by reference herein as if set forth in their entireties.

TECHNICAL FIELD

In one aspect, the present disclosure relates to dialysis catheters; and in particular, to systems and methods of cuffed and non-cuffed fenestrated dialysis catheters with abrasive tips.

BACKGROUND

Catheter systems typically include a hollow introducer needle, a flexible dilator slidably mounted over the needle, and a sheath slidably mounted over the dilator for successive insertion into a blood vessel or other biological liquid containing region of the human or animal body.

Central venous catheters are associated with a range of complications, which include the following: infection, malfunction, thrombosis, central venous stenosis, extremity edema, and the development of fibrin sheaths.

Catheter-related bloodstream infections alone have a reported incidence of 1.1 to 5.5 episodes per 1000 catheter days and are associated with increased morbidity, hospitalization, and death. Patients with indwelling catheters are further prone to develop infections. The longer the catheter dwells, the higher the likelihood it will get colonized by bacteria and eventually turn into a source of infection.

Central venous catheters (CVCs) are a common cause of nosocomial bacteremia among hemodialysis dependent subjects. National surveillance data indicate that incident and prevalent use of central venous catheters (CVCs) for hemodialysis vascular access exceeds current guideline recommendations in many jurisdictions. Infection is the second leading cause of death among hemodialysis patients, and use of CVCs as access is a predictor of all-cause and infection-specific mortality. Hemodialysis patients with a catheter have a two to three-fold increased risk of hospitalization for infection and death compared with patients with an arterio-venous fistula or graft. Treatment of Catheter related infections (CRT's) generally requires central venous catheters removal in most patient populations. However, patients undergoing hemodialysis are different from other patients with central venous catheters in several key aspects: (1) they have higher rates of venous thrombosis and stenosis that can lead to lack of future HD access sites, and (2) presence of a viable access site is literally a lifeline, especially in those patients who cannot tolerate long periods without dialysis.

There is a need to salvage venous access sites in these patients since catheter removal, on one hand, cannot allow reinsertion and thus, lead to loss of access site, and on the other hand, it cannot actually have a better outcome in terms of reinfection with the same organism.

There are essentially three routes for catheter bacterial colonization, which can lead to infections. First, skin bacteria tracking along catheter external surface, from catheter entry site, which is conventionally prevented by subcutaneous catheter tunneling, Dacron cuff, weekly sterile dressing changes, and use of antibiotic ointments at the entry site. The second route for catheter bacterial colonization includes direct contamination of catheter Hub health care worker or a contaminated infusate (fluid or medication). This route is conventionally prevented by use of maximum protection barriers, and antiseptic/antibiotic loaded caps in dialysis catheter hubs. The third route for catheter bacterial colonization is hematogenous seeding from another source of infection. Conventionally, there is no preventive approach, because prophylactic antibiotics are not recommended.

Catheter related infections (CRT's) typically require hospital admissions, IV antibiotics, and catheter management. With recurrent infections and repeated catheter removals/exchanges, patients eventually lose all venous accesses. CRI treatment is based on clinical presentation and is complex in hemodynamically unstable patients. If patient is hemodynamically unstable, the catheter is removed with delayed placement of a new tunneled catheter. There are 3 potential management options: systemic antibiotics alone; systemic antibiotics plus antibiotic lock; systemic antibiotics plus guidewire exchange.

Although there has been some improvement over the years, CRIs still are a common clinical problem and result in high costs health system. Dialysis catheters are still being removed in cases of infections and venous accesses permanently being lost. In patients with limited alternative venous access, catheters can be exchanged over a guidewire, to preserve the venous access while treating the infection.

There are two closely related issues that contribute to the failure of conventional approaches to prevent and treat CRIs: (1) bacterial colonization of subcutaneous tunnel with formation of biofilm along outer catheter shaft, which plays a major role in catheter infection, and (2) fibrin sheaths, which plays a major role in catheter malfunction. Since the pathogenesis of biofilm development to fibrin sheath formation is not well understood, there is debate as to the sequence of fibrin sheath formation, biofilm development, and their interdependency. However, the best evidence supports the hypothesis that a biofilm evolves over days to months into a more complex structure, i.e., a fibrin sheath. Fibrin sheaths are a complex of fibrin, collagen, and thrombus growth around a foreign body, which over the course of several weeks organizes into a fibrin sheath. They are reported to occur in to 50 to 100% of patients with central venous catheters.

Fibrin sheaths occur in 80 to 100% of all hemodialysis catheters within 1 week of insertion. The fibrin sheath initiates at the point of contact between the CVC and the vessel wall, advances along the entire length of the CVC or device, and can create a one-way valve mechanism, with resultant catheter malfunction. It has been reported that 50% of catheter malfunctions are the result of a fibrin sheath. Bacteria can embed themselves into the sheath, thereby increasing the risk of line-related infections and sepsis. Left alone, a fibrin sheath can persist months to years after catheter removal, and it is this longevity that can contribute to the increased risk of developing central venous stenosis after CVC usage. The association between fibrin sheaths, central stenosis, and SVC syndrome remains unexplored.

There is a paucity of therapies to prevent biofilm development and fibrin sheath formation. Accordingly, there is a need for catheter systems to prevent subcutaneous tunnel bacterial colonization and biofilm/fibrin sheath formation by allowing prophylactic pharmacologic treatment of the subcutaneous tunnel and outer catheter shaft with antithrombotic and antimicrobial locking solutions.

SUMMARY

The present disclosure provides catheter systems for temporary and prolonged use. In one embodiment, a catheter system is provided that includes a plurality of fenestrations along the shaft of the catheter. In this example, the fenestrations allow for continuous or intermittent infusion of antiseptics and/or antibiotics to prevent and treat bacterial colonization or infection of the subcutaneous tract. Exemplarily, the catheter system can include a third blind ended lumen in fluid communication with the fenestrations along a proximal shaft (subcutaneous portion) of the catheter for irrigation of antiseptics and/or antibiotics as needed to avoid outer catheter surface infections.

In embodiments, the catheter system can allow for treatment of patients with CRIs without abandoning venous access site (catheter salvage), by mechanical debridement of residual biofilm along subcutaneous tract and removal/stripping of fibrin sheath, thereby overcoming the disadvantages of the conventional systems. Exemplarily, the catheter system can include a removable coaxial stylet with an abrasive component in its tip to assist with mechanical debridement of subcutaneous tract and intravascular fibrin sheath during catheter placement.

Although the present disclosure describes catheters used for hemodialysis, it is contemplated the described catheter system can be used for any purpose, including, but not limited to, other tunneled catheters, such as, peritoneal dialysis, chest tubes for pleural effusions, peritoneal catheters for recurrent ascites, among others.

Exemplarily, the present disclosure provides a CRI treatment method. In this aspect, in an example of treatment of a patient with CRI, a conventional cuffed catheter should be exchanged over a guidewire for a fenestrated non-cuffed catheter. The replacement fenestrated non-cuffed catheter provides mechanical debridement of biofilm from subcutaneous tract and stripping of fibrin sheath. The fenestrations along the proximal shaft of the catheter enables chemical/pharmacological treatment of a colonized and/or infected subcutaneous tunnel, while the patient is also given systemic antibiotics. Optionally, placing a non-cuffed catheter in colonized or infected tunnels can minimize cellular or bacterial adhesion to the cuff fabric and facilitate treatment. Once infection resolves, the non-cuffed catheter can be exchanged over a guide wire for the fenestrated cuffed-catheter.

Exemplarily, the present disclosure provides a CRI prevention method. In this aspect, the use of modified fenestrated cuffed catheters allows the use of lock solutions and interventions to prevent or reduce biofilm and fibrin sheath formation. Commonly used lock solutions include, without limitation, heparin, citrate, EDTA, antibiotics such as aminoglycosides, and the like.

Optionally, the cuffed catheter can have at least one fenestration in the shaft adjacent but proximal to the Dacron cuff (between hubs and cuff) to allow irrigation of the segment of subcutaneous tunnel and the shaft lying between a patient's skin entry site and the cuff. The described systems and methods prevent biofilm and fibrin sheath growth. In contrast, conventional catheter designs have no way to prevent biofilm or fibrin sheath development. The described fenestrated tunneled catheters allow for intermittent or continuous infusion of chemical substances or antibiotics to treat the outer surface of the catheter and subcutaneous tunnel, via "subcutaneous tunnel locking".

Optionally, the described system can aid in preserving current venous access in patients diagnosed with CRI by exchanging the infected catheter for a fenestrated catheter that can be configured to be used to: (1) mechanically debride biofilm from subcutaneous tunnel; (2) mechanically strip fibrin sheath; and/or (3) disinfect and treat a colonized or infected tunnel.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Accordingly, these and other objects, along with advantages and features of the present invention herein disclosed, will become apparent through reference to the following description and the accompanying drawings. Furthermore, it is to be understood that the features of the various embodiments described herein are not mutually exclusive and can exist in various combinations and permutations.

BRIEF DESCRIPTION OF THE DRAWINGS

The accompanying drawings, which are included to provide a further understanding of the embodiments of the present disclosure, are incorporated in and constitute a part of this specification, illustrate embodiments of the present disclosure, and together with the detailed description, serve to explain the principles of the embodiments discussed herein. No attempt is made to show structural details of this disclosure in more detail than can be necessary for a fundamental understanding of the exemplary embodiments discussed herein and the various ways in which they can be practiced. According to common practice, the various features of the drawings discussed below are not necessarily drawn to scale. Dimensions of various features and elements in the drawings can be expanded or reduced to more clearly illustrate the embodiments of the disclosure.

Figures 5, 6:
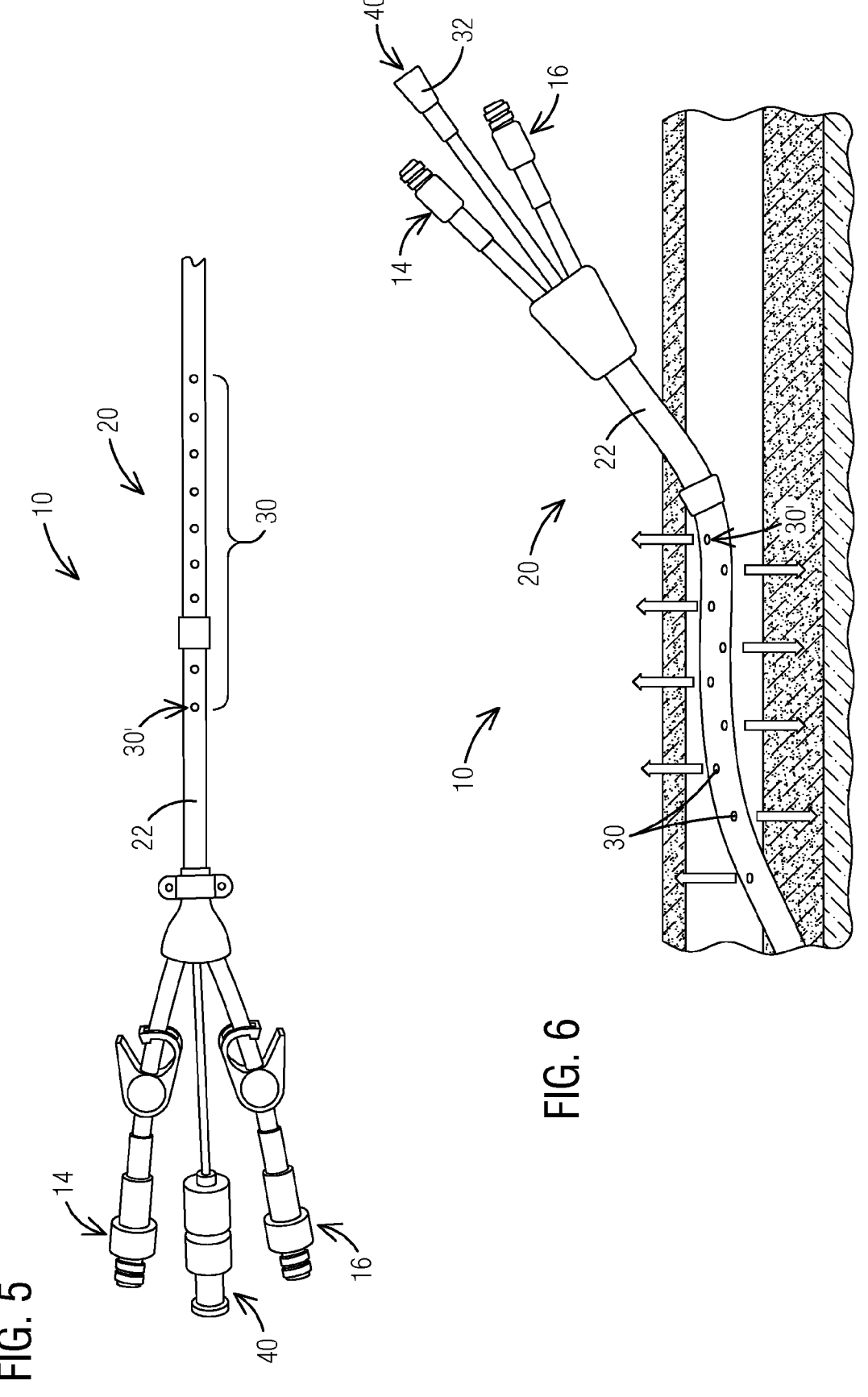

FIG. 5 is a schematic of an example of a cuffed catheter according to the present disclosure including a third port and irrigation holes along the shaft of the catheter.

FIG. 6 is a schematic of the cuffed catheter of FIG. 5, showing medicant being delivered via frustration, i.e., irrigation openings, along a proximal portion of the shaft of the catheter.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms “a,” “an” and “the” include plural referents unless the context clearly dictates otherwise. Thus, for example, reference to “a lumen” can include two or more such lumens unless the context indicates otherwise.

Ranges can be expressed herein as from “about” one particular value, and/or to “about” another particular value. When such a range is expressed, another aspect includes from the one particular value and/or to the other particular value. Similarly, when values are expressed as approximations, by use of the antecedent “about,” it will be understood that the particular value forms another aspect. It will be further understood that the endpoints of each of the ranges are significant both in relation to the other endpoint, and independently of the other endpoint.

As used herein, the terms “optional” or “optionally” mean that the subsequently described event or circumstance can or cannot occur, and that the description includes instances where said event or circumstance occurs and instances where it does not.

The word “or” as used herein means any one member of a particular list and also includes any combination of members of that list. Further, one should note that conditional language, such as, among others, “can,” “could,” “might,” or “can,” unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular embodiment.

The phraseology and terminology used herein is for the purpose of description and should not be regarded as limiting. As used herein, the term “plurality” refers to two or more items or components. The terms “comprising,” “including,” “carrying,” “having,” “containing,” and “involving,” whether in the written description or the claims and the like, are open-ended terms, i.e., to mean “including but not limited to.” Thus, the use of such terms is meant to encompass the items listed thereafter, and equivalents thereof, as well as additional items. Only the transitional phrases “consisting of” and “consisting essentially of,” are closed or semi-closed transitional phrases, respectively, with respect to any claims. Use of ordinal terms such as “first,” “second,” “third,” and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish claim elements.

Disclosed are components that can be used to perform the disclosed methods and systems. These and other components are disclosed herein, and it is understood that when combinations, subsets, interactions, groups, etc. of these components are disclosed that while specific reference to each various individual and collective combinations and permutation of these cannot be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems can be understood more readily by reference to the following detailed description of preferred embodiments and the examples included therein and to the Figures and their previous and following description.

In one embodiment, the catheter system 10 can include a dialysis catheter 20 with fenestrations 30, i.e., openings, defined along a shaft 22 to allow for continuous or intermittent infusion of antiseptics and/or antibiotics for preventing bacterial colonization or treating or infections of the subcutaneous tract. In a further aspect, the dialysis catheter 20 can also include removable component (stylet or guidewire) with an abrasive tip to assist with mechanical debridement of subcutaneous tract and intravascular fibrin sheath during catheter placement.

Exemplarily, the present disclosure provides a catheter 20, which includes, without limitation, non-cuffed and cuffed catheter types. Both catheter types include a shaft 22 of suitable length to facilitate placement within the patient. It is contemplated that the shaft 22 can be linear or curved shape suitable for stabilizing the catheter inside the patient for longer periods of time.

Optionally, the catheter 20 (cuffed and/or non-cuffed catheter) can include a third blind ended lumen 32 to the dialysis catheter that fluidly connects with the fenestrations 30 (e.g., holes, openings, irrigation ports, etc.) along the shaft of the catheter to allow for selective infusion/irrigation

7 of antiseptics (e.g., EDTA and the like) and/or antibiotics as frequently as needed to avoid outer catheter surface and subcutaneous tract bacterial colonization (i.e., "subcutaneous tunnel locking"). The fenestrations 30 re configured to maintain the subcutaneous tunnel and outer catheter surface bacteria free. In operation, the blind end lumen 32 and proximally located fenestrations 30' can decrease the amount of antiseptic and/or antibiotics that reaches the blood stream. In an example, and as shown in FIG. 5, the cuffed catheter 20 can include at least one hole/opening 30' proximal to the cuff to allow for disinfection of a segment of the catheter/tunnel that extends from the skin entry site to the cuff.

Figures 1A, 1B:
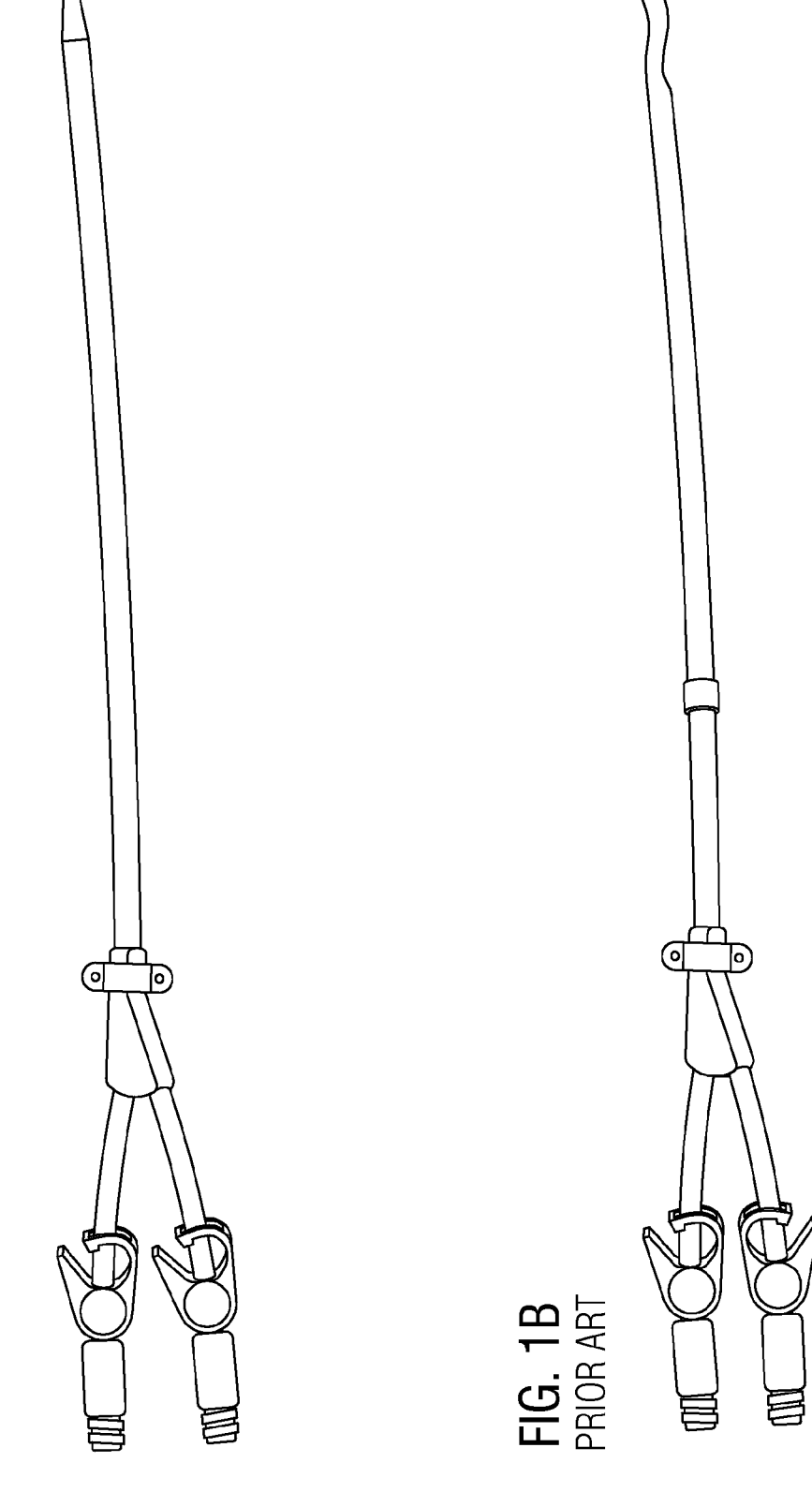
FIG. 1A is a schematic of a conventional non-cuffed catheter.
FIG. 1B is a schematic of an example of a conventional cuffed catheter.

As shown in FIGS. 1A and 1B, most common dialysis catheters designs have two dissimilarly sized ports that are fused together. During dialysis, blood is aspirated from one port of the catheter, is communicated via the catheter to a dialysis machine for treatment, and is subsequently returned back to the patient via the catheter back into the patient via the second port. At the end of every session (e.g., triweekly) each port is conventionally locked with a locking solution, such as Heparin.

The present system can be configured to include a third port 40 that is in communication with an outer lumen that can be shorter than the noted interior lumen(s) of the two dissimilarly sized ports. The outer lumen in communication with the third port can be blind ended so that the third port 40 does not reach or otherwise substantially fluidly communicate with the vein lumen. In this aspect, it is contemplated that the third port 40 is connected to the holes or fenestrations 30 along the proximal portion of the shaft of the catheter. Thus, as shown in FIG. 6, a solution dispersed from the third port 40 will be dispensed into the symptomatic or asymptomatic patient through the fenestrations 30 and outside the catheter. It is contemplated that some of the solution or medicant dispensed via the third port can be reabsorbed by soft tissues and some can track retrogradely or track along the shaft 2 in an antegrade fashion and to enter the vein lumen (systemic leak).

In an example, the catheter 20 includes an outer wall and inner wall, wherein the outer wall includes a plurality of fenestrations 30. The interior cavity defined by the inner wall is the interior lumen. The space between the outer wall and inner wall is the outer lumen. At least one port, e.g., the first and second ports 14 and 16, can be in fluid communication with the inner lumen. In the present system, the third port 40 can be in fluid communication with the outer lumen, such that antibiotics and/or antiseptic can be distributed into the outer lumen and dispensed via the fenestrations 30 to prevent infections related to the catheter.

A fibrin sheath is known to build-up around the indwelling access of the catheters. Typically, a fibrin sheath initiates at the point of contact between the catheter, advances along the entire length of the catheter, and can create a one-way valve mechanism, with resultant decrease in the catheter flow. As noted above, fibrin sheaths play a major role in CVC malfunction. The conventional approach is to replace catheters over guidewires without or with fibrin sheath balloon stripping. In an example, the catheter can include a removable over-the-wire stripping apparatus for removing a fibrin sheath from the outlet end of the catheter disposed in a patient's vascular system.

Figures 2, 3A, 3B:
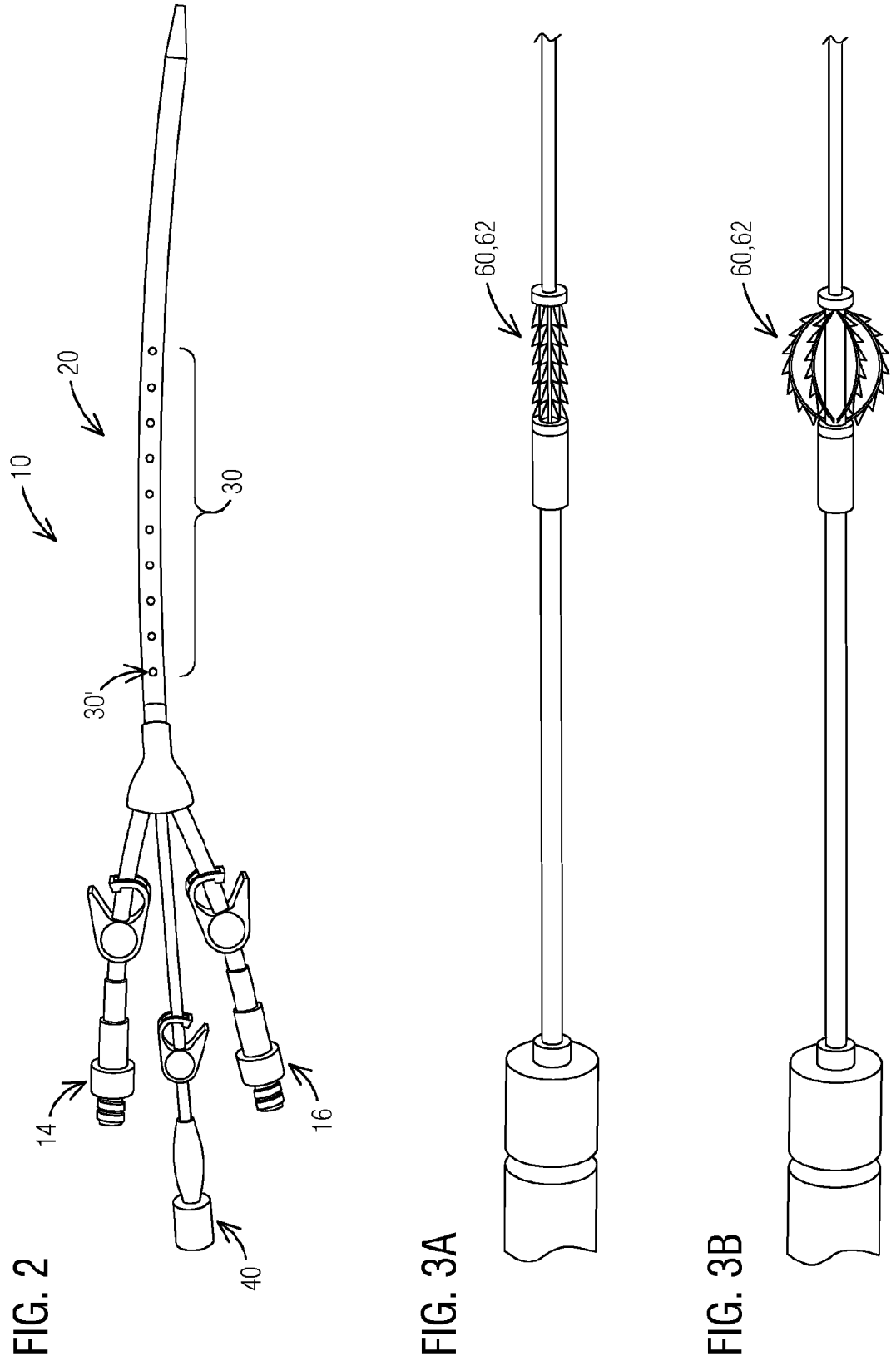
FIG. 2 is a schematic of an example of a non-cuffed catheter according to the present disclosure including a $3^{rd}$ blind ended port that communicates with a plurality of irrigation holes along the shaft of the catheter.
FIG. 3A is a schematic of an example of a non-cuffed catheter of FIG. 2, with a removable over-a-wire stylet with abrasive tip.
FIG. 3B is a schematic of an example of the non-cuffed catheter of FIG. 3A, wherein the removable over-a-wire stylet with abrasive tip is a metal cage, which can be self-expandable operator actuated.
Figures 3C, 4A, 4B:
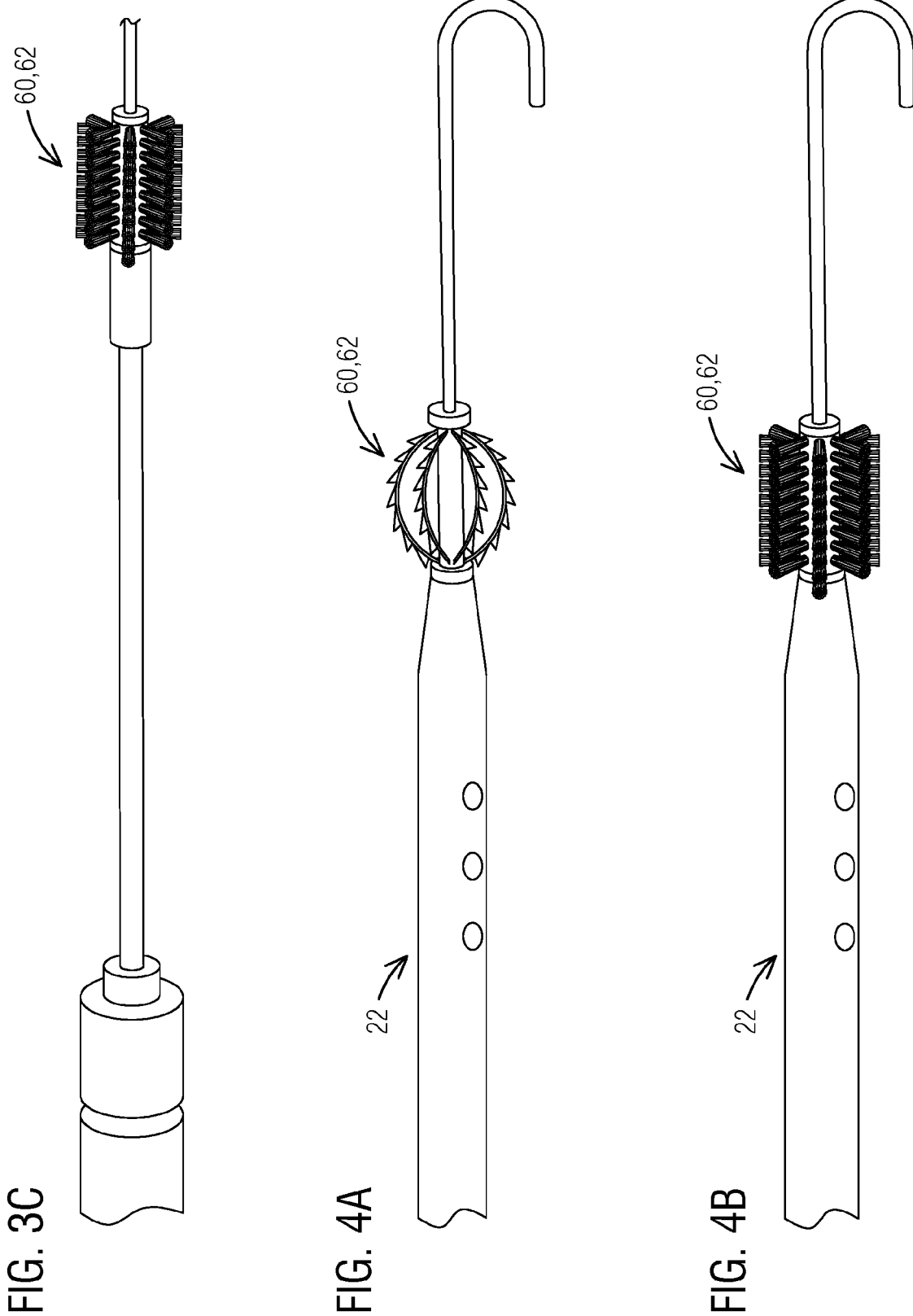
FIG. 3C is a schematic of an example of the non-cuffed catheter of FIG. 3A, wherein the removable over-a-wire stylet with abrasive tip is brush. In such example, the brushed type of abrasive tip can include a sheath covering the brush tip, wherein upon removal of the sheath, the brush is exposed to hold the position of the catheter in place.
FIG. 4A is a schematic of an example of the non-cuffed catheter of FIG. 2, including an expandable abrasive tip.
FIG. 4B is a schematic of an example of the non-cuffed catheter of FIG. 2, including a brush type abrasive tip.

In contrast, in order to remove the fibrin sheath in a symptomatic or asymptomatic patient, the catheter 20 of the disclosed system can include a collapsible and removable abrasive component 60 at the distal tip of the catheter. For example, and referring to FIGS. 3A and 4A, a catheter including an expandable abrasive tip 62 is shown. Optionally, and referring to FIGS. 3B and 4B, an exemplary catheter that includes a brush type abrasive tip is illustrated. The abrasive tip 62 can be used to maintain position of the catheter once inserted, and can mechanically remove dead tissue, debris, biofilm, and fibrin sheath. The abrasive tip 2 of the catheter aids with mechanical debridement of contaminated and/or adherent tissue from a subcutaneous tunnel.

In an example, the abrasive component 60 of the catheter can be rotatable for removing material from the vessels of a symptomatic or asymptomatic patient, such as the fibrin sheath, wherein the abrasive component can remove hardened atherosclerotic materials without damaging the normal elastic soft tissue of the vessel wall. For example, the rotating component can include a circumferentially spaced flange extending radially outward from the body (e.g., brush like, cage like, etc.). The catheter can optionally include an outer housing and inner housing, in which an abrasive component is attached to the external surface of the outer housing and in which the outer housing is configured to selectively rotate about the inner housing.

Optionally, the abrasive tip 62 can be configured to be selectively separated from the catheter and can be sized or otherwise shaped to be coaxially advanced over the wire through the dialysis catheter hub, and to be subsequently advanced through the dialysis catheter shaft and out the distal end of the catheter. In optional aspects, it is further contemplated that the abrasive tip can serve as a catheter stiffening stylet with a brush, cage, or the like in its distal tip.

In one non-limiting example, a fully expanded or unconstrained abrasive tip 62 can have a diameter that is larger than the outer catheter diameter, which allows for: (1) creation of enough friction with walls of subcutaneous tunnel, allowing tissue debridement; and (2) when located within a vein, have a larger diameter than that of the intravascular fibrin sheath, allowing for fibrin sheath stripping.

In a further non-limiting example, a previously placed catheter is removed over a guide wire. A non-cuffed catheter of the present system can then be loaded over the wire, wherein the abrasive tip leads the catheter while it is advanced into the vessel. Friction from the abrasive tip can cause some degree of debridement of subcutaneous tunnel tissues. When the abrasive tip reaches vessel lumen it can be selectively expanded to aide in stripping fibrin sheath as the catheter is advanced over the wire. When the non-cuffed catheter of the present system has reached the desired position, the stylet with abrasive tip and guiding wire can be pulled out and removed from the catheter.

As noted above, it is contemplated that the catheter system can include two injection port. (e.g., in communication with the inner catheter) that can be used to aspirate or inject blood during dialysis or to deliver saline or other fluids into the inner catheter. And, as noted above, it is contemplated that the catheter system can include a third port that can be for subcutaneous irrigation (e.g., a port in communication with the outer catheter and fenestrations) to direct medications into the outer catheter. In an example, the medicant or medications can include, without limitation, antiseptics, antibiotics, antiplatelets, anticoagulants, thrombolytics, and the like. Optionally, injected medications could be in gel form, to make them last longer (e.g., slow release formulations) and stay confined to subcutaneous track after applied. It is also contemplated that the third port can be used to inject other drugs such as: pro-coagulants (thrombin) in case of bleeding/oozing after new catheter placement or catheter exchange. Further, it will be appreciated that subcutaneous tunnel locking can be selectively performed by irrigating the patient via the third port and fenestrations, utilizing biocompatible solutions such as, for example and without limitations, Vashe®Wound solution, Dakin's® Solution, and the like.

The present system provides a method of use of the disclosed modified non-cuffed and cuffed dialysis catheters. In the event of a CRI, the old indwelling cuffed catheter is exchanged for a modified non-cuffed catheter through the same subcutaneous track. Once the CRI is treated, the indwelling modified non-cuffed catheter can be exchanged over a guidewire for a modified cuffed catheter. All new patients requiring a tunneled dialysis catheter can be offered a modified cuffed catheter as the standard of care.

It should be emphasized that the above-described aspects are merely possible examples of implementations, merely set forth for a clear understanding of the principles of the present disclosure. Many variations and modifications can be made to the above-described embodiment(s) without departing substantially from the spirit and principles of the present disclosure. All such modifications and variations are intended to be included herein within the scope of the present disclosure, and all possible claims to individual aspects or combinations of elements or steps are intended to be supported by the present disclosure. Moreover, although specific terms are employed herein, as well as in the claims which follow, they are used only in a generic and descriptive sense, and not for the purposes of limiting the described invention, nor the claims which follow.

What is claimed is:

1. A catheter system to treat a symptomatic or asymptomatic patient, comprising:
a catheter having a shaft formed by an outer wall and a spaced inner wall, wherein the inner wall defines an interior lumen that extends to a distal end of the shaft that is configured to be positionable within a vein lumen of the patient and that is in fluid communication with a first port and a second port, wherein space between the outer wall and the inner wall defines a blind ended outer lumen in fluid communication with a third port, wherein the interior lumen and the blind ended outer lumen are configured to prevent fluid communication therebetween, wherein an outer surface of the outer wall of the catheter defines a plurality of fenestrations positioned on a proximal portion of the shaft that is in fluid communication with the blind ended outer lumen, wherein the third port is in fluid communication with a medicant deliverable to the patient via the plurality of fenestrations, wherein the plurality of fenestrations is spaced remotely from the distal end of the shaft at a distance sufficient to prevent medicant delivered via the plurality of the fenestrations from entering the vein lumen of the patient, and wherein the plurality of fenestrations is in communication with a subcutaneous tract of tissue surrounding the proximal portion of the shaft of the catheter to maintain a portion of the outer catheter surface and the subcutaneous tract proximate the proximal portion shaft of the catheter bacteria free.

2. The catheter system of claim 1, wherein the catheter is a cuffed catheter having a cuff positioned on the proximal portion of the shaft.

3. The catheter system of claim 1, wherein the shaft of the catheter includes a first at least one fenestration of the plurality of fenestrations positioned proximal to the cuff to allow for disinfection of a segment of the catheter along a portion of the subcutaneous tract adjacent to the first at least one fenestration, and wherein the shaft of the catheter includes a second at least one fenestration of the plurality of fenestrations positioned distal to the cuff to allow for disinfection of a segment of the catheter along a portion of the subcutaneous tract adjacent to the second adjacent to the second at least one fenestration, wherein the second at least one fenestration distal to the cuff is spaced from the distal end of the shaft.

4. The catheter system of claim 1, wherein the catheter is a non-cuffed catheter.

5. The catheter system of claim 1, wherein the shaft has a shape that is configured to be linear and/or curved shape for stabilizing the catheter inside the patient.

6. The catheter system of claim 1, wherein the medicant is an antibiotic.

7. The catheter system of claim 1, wherein the medicant is an antiseptic.

8. The catheter system of claim 1, wherein the outer lumen is shorter than the interior lumen.

9. The catheter system of claim 1, wherein the blind ended outer lumen prevents the third port from being in fluid communication with the vein lumen of the patient.

10. The catheter system of claim 1, further comprising an abrasive component on an outer surface of the outer wall of the catheter proximate the distal tip of the catheter.

11. The catheter system of claim 1, further comprising an expandable abrasive component on an outer surface of the outer wall of the catheter proximate the distal tip of the catheter.

12. The catheter system of claim 1, further comprising a collapsible and removable abrasive component on an outer surface of the outer wall of the catheter proximate the distal tip of the catheter.

13. A catheter system to treat a symptomatic or asymptomatic patient, comprising:
a cuffed catheter having a cuff positioned on a proximal portion of a shaft, wherein the shaft is formed by an outer wall and a spaced inner wall, wherein the inner wall defines an interior lumen that extends to a distal end of the shaft that is configured to be positionable within a vein lumen of the patient and that is in fluid communication with a first port and a second port, wherein space between the outer wall and the inner wall defines a blind ended outer lumen in fluid communication with a third port, wherein the interior lumen and the blind ended outer lumen are configured to prevent fluid communication therebetween, wherein an outer wall surface of the outer wall of the catheter defines a plurality of fenestrations on a proximal portion of the shaft that is in fluid communication with the blind ended outer lumen, wherein the third port is in fluid communication with a medicant deliverable to the patient via the plurality of fenestrations, wherein the plurality of fenestrations is spaced from the distal end of the shaft at a distance sufficient to prevent medicant delivered via the plurality of the fenestrations from entering the vein lumen of the patient, wherein the plurality of fenestrations is in communication with a subcutaneous tract of tissue surrounding the proximal portion shaft of the catheter to maintain the outer catheter surface and subcutaneous tract proximate the proximal portion shaft of the catheter bacteria free, wherein the shaft of the cuffed catheter includes a first at least one fenestration of the plurality of fenestrations that is positioned proximal and adjacent to the cuff to allow for disinfection of a portion of outer catheter surface of the catheter adjacent to the first at least one fenestration, and wherein the shaft of the catheter includes a second at least one fenestration of the plurality of fenestrations that is positioned distal and adjacent to the cuff to allow for disinfection of a portion of outer catheter surface of the catheter adjacent to the second at least one fenestration.

14. The catheter system of claim 13, wherein the medicant is an antibiotic.

15. The catheter system of claim 13, wherein the medicant is an antiseptic.

16. The catheter system of claim 13, wherein the outer lumen is blind ended so that the third port is not in fluid communication with the vein lumen of the patient.

* * * * *